(12) United States Patent
Landegren

(10) Patent No.: US 7,351,528 B2
(45) Date of Patent: *Apr. 1, 2008

(54) PROBING OF SPECIFIC NUCLEIC ACIDS

(75) Inventor: Ulf Landegren, Uppsala (SE)

(73) Assignee: Olink AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/029,913

(22) Filed: Dec. 31, 2001

(65) Prior Publication Data

US 2002/0102592 A1 Aug. 1, 2002

Related U.S. Application Data

(62) Division of application No. 09/171,935, filed on Apr. 27, 1999, now abandoned.

(30) Foreign Application Priority Data

Apr. 30, 1996 (SE) .................................... 9601676
Apr. 30, 1996 (WO) ..................... PCT/SE97/00737

(51) Int. Cl.
C12Q 1/68 (2006.01)
C07H 21/04 (2006.01)
C12M 1/36 (2006.01)

(52) U.S. Cl. .................... 435/6; 435/91.1; 435/287.2; 536/23.1; 536/24.3

(58) Field of Classification Search ................... 435/6, 435/91.2, 91.52, 810, 320.1; 436/501; 935/23, 935/78, 88; 536/27, 23.4; 530/350, 23.4
See application file for complete search history.

(56) References Cited

U.S. PATENT DOCUMENTS

| | | | | |
|---|---|---|---|---|
| 5,124,246 A | * | 6/1992 | Urdea | 435/6 |
| 5,427,930 A | * | 6/1995 | Birkenmeyer | 435/91.52 |
| 5,643,724 A | * | 7/1997 | Fildes | 435/6 |
| 5,871,921 A | * | 2/1999 | Landegren | 435/6 |
| 5,952,176 A | | 9/1999 | McCarthy et al. | 435/6 |

FOREIGN PATENT DOCUMENTS

WO WO 95/22623 * 8/1995

OTHER PUBLICATIONS

Nilsson et al., "Padlock Probes: circularizing oligonucleotides for localized DNA detection", Science, (Sep. 30, 1994), vol. 265, pp. 2085-2088.*
Nilsson et al. "Padlock probes: Circulating oligonucleotides for localized DNA detection", Science vol. 265, pp. 2085-2088.
Stratagene catalog, p. 39.

* cited by examiner

*Primary Examiner*—B J Forman
(74) *Attorney, Agent, or Firm*—Young & Thompson

(57) ABSTRACT

The present invention relates to improved methods for probing of specific nucleic acids using circularizable probes designed such that they report the presence of a target sequence by allowing a detectable moiety to remain bound if an only if the probe has been cyclized in a target-dependent linking reaction. The invention may be used for distinction between sequence specific variations of nucleic acids.

10 Claims, 2 Drawing Sheets

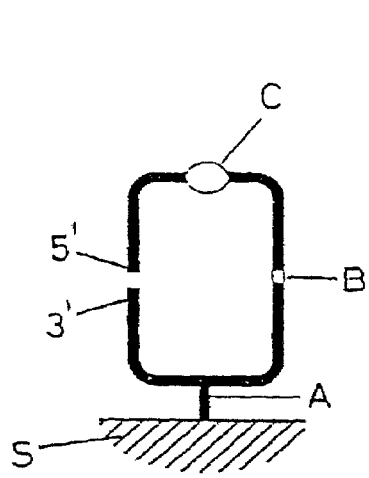
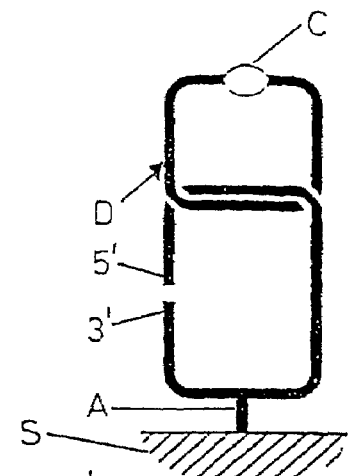
FIG. 1  FIG. 2
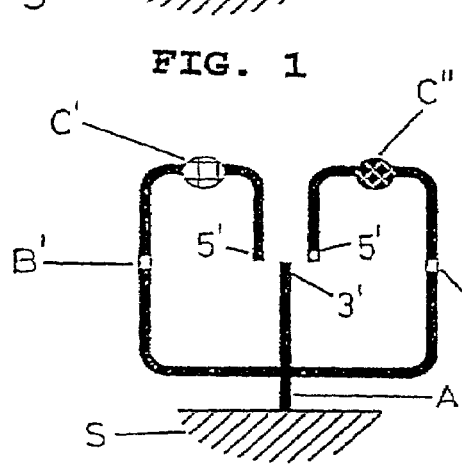
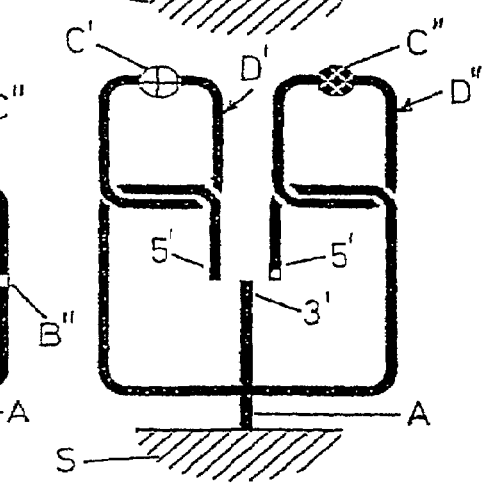
FIG. 3  FIG. 4
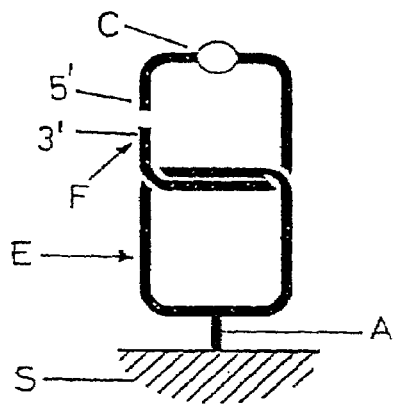
FIG. 5

```
C(NH2)TTTTTTATAATGTTAAGTGACCGGCAGCAAAAATGTTUT
T                                             T
T                                             U
T            Padlock FV                       T
T                                             T
T                                             U
T                                             T
A                                             T
GCAGATCCCTGGACAGGCG-3'  5'-AGGAATACAGGTACTTTTU

3'-TCGTCTAGGGACCTGTCCGCTCCTTATGTCCATGAAAAA-5'

Oligo FV
```

FIG. 6

```
TTTTTTTTTTTTTTTTTTTTC(NH2)TTTTTTTTTTTTTTTTTTTT
T                                             T
T                                             T
T                                             T
T            Padlock αFV                      T
T                                             T
T                                             T
T                                             G
TGATCGTATTACAATTCACTG-3'  5'-GCCGTCGTTTTACAAGTT C(NH2)TTTTTTATAATGTTAAGTGACCGGCAGCAAAAATGTTUT
T                                             T
T                                             U
T            Padlock FV                       T
T                                             T
T                                             U
T                                             T
A                                             T
GCAGATCCCTGGACAGGCG-3'  5'-AGGAATACAGGTACTTTTU

3'-TCGTCTAGGGACCTGTCCGCTCCTTATGTCCATGAAAAA-5'

Oligo FV
```

FIG. 7

SEQUENCE LISTING

```
<160> NUMBER OF SEQ ID NOS: 3

<210> SEQ ID NO 1
<211> LENGTH: 93
<212> TYPE: DNA
<213> ORGANISM: Artificial Sequence
<220> FEATURE:
<223> OTHER INFORMATION: Description of Artificial Sequence: Synthetic
      DNA/RNA hybrid
<223> OTHER INFORMATION: Description of Combined DNA/RNA Molecule:
      Synthetic DNA/RNA hybrid

<400> SEQUENCE: 1
aggaatacag gtactttttu ttuttuttut tgtaaaaacg acggccagtg aattgtaata    60
```

```
tttttctttt tttagcagat ccctggacag gcg                          93

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aaaaagtacc tgtattcctc gcctgtccag ggatctgct                    39

<210> SEQ ID NO 3
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gccgtcgttt tacaagttgt tttttttttt tttttttttt ttttctttt tttttttttt    60 tttttttttt ttgatcgtat tacaattcac tg                           92
```

PROBING OF SPECIFIC NUCLEIC ACIDS

TECHNICAL FIELD

The present invention relates to improved methods for probing of specific nucleic acids. More specifically, the invention relates to a method of detecting specific nucleic acid sequences as well as probes and detecting kits therefor.

BACKGROUND OF THE INVENTION

Detection of unique target sequences in the complexity of the human genome requires highly specific detection reagents. This form of gene detection permits target sequence variants to be screened for and it represents one of the most important modalities of gene analysis. The hybridization of single oligonucleotides in general does not afford the requisit specificity, while the combination of two probes such as in PCR (polymerase chain reaction) or OLA (oligonucleotide ligation assay) allows specific detection of unique target sequences.

In situations where many different target sequences are investigated together in a sample by techniques such as PCR or OLA, the risk of "crosstalk" between noncognate pairs of probes, giving rise to false detection signals, increases exponentially with multiplexing.

WO 95/22623 discloses a probe designed to be circularized in the presence of a target sequence and caused to close around the target-containing nucleic acid strand such that the cyclic probe will interlock with and thereby be efficiently linked to the target nucleic acid to be detected. Because of the helical nature of double-stranded nucleic acids, such as DNA, circularized probes will be wound around the target strand, topologically connecting probes to target molecules through catenation, in a manner similar to a padlock. Such covalent catenation of probe molecules to target sequences results in the formation of a hybrid that resists extreme washing conditions, serving to reduce non-specific signals in genetic assays. Any probes hybridizing in a non-specific manner may therefore be removed by subjecting the target to non-hybridizing conditions and/or exonuclease activity. Provided that the circular probe is properly detectable, such as by being suitably labelled, it may then be detected to indicate the presence of the target molecule.

In an assay based on such circularizable probes only intramolecular reactions give rise to a signal, thereby greatly improving the potential for multiplexing.

SUMMARY OF THE INVENTION

The present invention relates to improved methods of detecting specific nucleic acid sequences by means of circularizable probes as well as detecting kits and probes therefor giving considerable advantages in specificity, noise reduction and kinetics compared to prior art.

According to the invention, the circularizable probes are designed such that they report the presence of a target sequence by allowing a detectable moiety to remain bound if and only if the probe has been cyclized in a target-dependent linking reaction.

Thus, in a first aspect, the invention provides a method of detecting a target nucleic acid sequence in a sample by contacting the sample with a detectable probe to hybridize the probe to the target sequence, and detecting the hybridized probe, said probe (below called padlock probe) having two free nucleic acid end parts which are at least partially complementary to and capable of hybridizing to two at least substantially neighbouring regions of the target sequence. The method comprises the following steps: a) hybridizing the probe ends to the target sequence under hybridizing conditions; b) covalently connecting the ends of the hybridized probe with each other to form a circularized structure; c) washing under denaturating conditions. The method is characterized in that one end part of the probe is provided with a cleavable or dissociable detectable function, and the method comprises the further steps of: d) cleaving or dissociating said detectable function; e) separating probes with connected ends from probes with non-connected ends by washing under denaturing conditions; and f) detecting the presence and, if desired, location of the remaining probe as indicative of the presence of the target nucleic acid sequence.

The detectable function can be cleavable by being connected to the remainder of the probe via a cleavable site or linker located on the same probe end as the detectable function.

A dissociable detectable function can be provided on second padlock probe having two free nucleic acid end parts which are at least partially complementary to and capable of hybridizing to two at least substantially neighbouring regions of the first probe sequence. Such a second padlock probe can be added to the probe either before or after the probe has been reacted with the target sequence. It is also possible to provide the dissociable detectable function on the target-sequence specific probe if the second padlock probe is immobilized to a support.

In one embodiment of the method, the padlock probe has two linear probe ends. One of the probe ends contains a detectable function which is capable of being either cleaved off or dissociated from the probe end.

In another embodiment of the method, at least one of the probe ends of the padlock probe is branched, e.g. with up to ten branches or even more, and a cleavable or dissociable detectable function is provided on each of the branches or arms. The branch ends may be specific for the respective sequence variants to be distinguished in the assay, for instance to identify allelic sequence variants or to perform a quantitative comparison between similar sequences. Preferably, only one of the probe ends is branched, especially bifurcated.

In the method according to the present invention, the covalent linking or connecting between two ends of a probe anchors a detectable signal. If no linking has ocurred, the signal will not be detected. Examples of preferred signals are fluorophores, radioisotopes, haptens, enzymes etc.

The covalent connection of the probe ends to each other after hybridization to the target sequence may be performed by enzymatic, ribozyme-mediated or chemical ligation, preferably enzymatic ligation.

Instead of letting the probe ends hybridize in juxtaposition to the target sequence, the probe may be designed to hybridize to the target molecule such that an interspace is left between the probe ends, and that at least one additional probe is provided which is designed to hybridize to the target molecule in this interspace, whereupon the hybridized probes are covalently interconnected.

Optionally, the probe or probes are designed to hybridize to the target molecule to leave a small gap between adjacent probe ends. This gap or gaps are then filled by an extension reaction prior to covalently interconnecting the probe ends.

The method of the invention may particularly be used for detecting, quantifying and distinguishing between sequence variants with regard to one or several target sequences in a sample. Examples of applications include distinction between normal and mutated sequence variants, associated with disease, genetic linkage analysis of biallelic markers, and quantification of gene expression in a tissue sample.

In a second aspect of the invention, there is provided a kit for detecting a target nucleic acid sequence in a sample, comprising a) a padlock probe having two free nucleic acid end parts which are at least partially complementary to and capable of hybridizing to two at least substantially neighbouring regions of the target sequence; and b) a means for connecting the ends to each other after hybridization to the target sequence. The kit according to the invention is characterized in c) a cleavable or dissociable detectable function; and, optionally, d) a cleaving agent.

In one embodiment of the kit, the padlock probe has two linear probe ends, one of the probe ends containing a detectable function which is cleavable or dissociable.

In another embodiment of the kit, at least one of the two free nucleic acid end parts of the padlock probe is branched, e.g. with up to ten branches or even more, and each of the branches or arms is provided with a different detectable function. Preferably, only one of the probe ends is branched, especially bifurcated.

In a third aspect, the present invention provides for use of the above kit for distinction between sequence-specific variants of nucleic acids, such as allele-specific variants.

In a fourth aspect, there is provided a padlock probe having two free nucleic acid end parts which are at least partially complementary to and capable of hybridizing to two at least substantially neighbouring regions of the target sequence, and at least one cleavable or dissociable function on one of the end parts of the probe.

In a fifth aspect there is provided a padlock probe having two free nucleic acid end parts, where at least one of the two end parts is branched.

DETAILED DESCRIPTION OF THE INVENTION

The invention will now be described in more detail below in association with the accompanying drawings, in which FIG. 1 shows a monospecific cleavable detectable probe;

FIG. 2 shows a monospecific dissociable detectable probe;

FIG. 3 shows a bispecific cleavable detectable probe having differentially labelled sequence variant-specific and cleavable probe branches;

FIG. 4 shows a bispecific dissociable detectable probe having differentially labelled sequence variant-specific secondary padlock probes, attached to sequence variant-specific branches;

FIG. 5 shows a variant of a monospecific dissociable detectable probe where the detectable function is provided on the target-sequence specific probe;

FIG. 6 shows the DNA sequences of a cleavable padlock probe (SEQ ID NO: 1) and a complementary target sequence (SEQ ID NO: 2); and FIG. 7 shows the two DNA sequences in FIG. 6 (SEQ ID NOS: 1-2) together with the DNA sequence (SEQ ID NO: 3) of a padlock probe complementary to the back-piece of the cleavable padlock probe.

In FIG. 1, two probes terminating with free 3' and 5' ends, respectively, are immobilized together on a support S via a solid phase anchor A. One of the arms also includes a breakable link to the support in the form of a cleavable linker B, and, farther away from the support, a detectable function C such as a fluorophore. Examples of cleavable links and cleaving agents include disulphides, cleavable by reducing agents such as dithiothreitol, deoxyuridine residues, cleavable by uracil DNA glycosylase; peptide residues cleavable by peptidases and nucleotide sequences susceptible to cleavage by endonucleases.

As an alternative to a support-bound format, it is possible to perform the hybridization-ligation reactions in solution, followed by an immobilization or separation reaction.

If the two ends hybridize in juxtapositon on a target sequence, then they can become joined by an act of template-dependent ligation and thereby catenated to the target sequence as described in more detail in the above-mentioned WO 95/22623 (the disclosure of which is incorporated herein by reference). After the hybridization-ligation reaction, the cleavable linker is broken and the support is washed vigorously. Any remaining detectable group indicates that this has become joined to the support via the other probe arm. The probe thus functions as a logic "OR" gate, giving a positive answer as long as one or both of the links to the support are intact.

In FIG. 2, the probes are constructed such that a secondary, detectable padlock probe D is allowed to circularize around the back-piece of a specific target detection padlock probe, bound to the support. If and only if this specific probe interacts with its target and is cyclized, then the detectable padlock probe will remain bound to the support after denaturing washes.

If the probes are used for distinction of sequence variants, such as allele distinction reactions, then the detection probes can be designed as shown in FIGS. 3 and 4 to include a single 3' end and at the other end branching into two allele-specific 5' ends (or the other way around). In this design the sequence variant-specific probe segments can be designed to hybridize with lesser stability and they each have distinct cleavable, C', C", or dissociable detectable, C', D', C", D", functions. In this manner all target sequences can give rise to a signal but only from that sequence variant-specific probe that hybridizes and ligates the best.

FIG. 5 shows an alternative embodiment of monospecific dissociable detectable probe to that shown in FIG. 2. While in FIG. 2, the target-sequence specific probe is in immobilized and linked to the non-specific signal-generating padlock probe, D, the embodiment shown in FIG. 5 has the non-specific probe, E, immobilized and the detectable probe F is also target-sequence specific.

While in FIGS. 1 to 5 the cleavable linker and the detectable function are shown provided on the 5' end arm or arms, the 3' and 5' ends may, of course, be reversed.

Assays of the above type suffer no risk of crosstalk with increasing probe numbers as only intramolecular reactions are possible or detectable, extreme background reduction is possible through denaturing washes allowing convenient detection of thousands or less of target molecules, and excellent allele-distinction is obtained through the (competitive) ligation reactions.

The methods of the invention can be be performed on immobilized target sequences, such as metaphase chromosomes. Following the ligation and washes at or above stringency, the probes are opened and the reaction washed resulting in the disappearance of free ends, but ends connected via hybridization retain their binding with the target sequence.

While conventional linear hybridization probe arrays lack the specificity and background-reduction possibility required to analyze complex DNA samples, probes according to the invention avoid both of these limitations. However, one important difficulty of using complex samples as templates remain, viz. it is important to arrange the assay so that a DNA sample (preferably sheared or otherwise reduced in average size) is brought in close contact with all positions in a probe array. For this reason, one-dimensional probe arrays are envisioned for this purpose. These could be separate segments of channels or tubes through which the DNA sample is serially passed. It is also possible to use the principle of "stacking and sectioning" previously described in the international patent application WO 96/17246 (the disclosure of which is incorporated herein by reference) to create one-dimensional probe arrays of this type.

The following non-limiting Examples illustrate the invention further.

EXAMPLE 1

Detection Principle (FIG. 1)

The detection principle is based upon that described above with regard to FIG. 1. A padlock probe of a defined specificity (below to Factor V) is synthesized with a few thymine (T) bases replaced by uracil (U) bases and is covalently immobilized to a surface or immobilized via biotin to a streptavidin-coated surface. Beyond the coupling site to the surface the padlock probe has a detectable tag, e.g. a fluorophore, and the uracil-containing part. The padlock probe is hybridized and ligated to its template and treated with the enzyme uracil DNA glycosylase (UDG). UDG cleaves off the uracil bases from the padlock probe to leave the phosphodiester bond.

This abasic binding is unstable and is easily broken by heat, basic pH or Exonuclease III. If ligation has taken place, the tag signal will remain after wash, but if no ligation has taken place, the signal tag may be washed away since that part of the padlock probe is no longer connected to the rest of the probe and is thereby not attached to the surface.

UDG-cleavage of U-containing DNA (In Solution)

0.1 pmole of 92-mer padlock probe to Factor V (Padlock FV, FIG. 6), $^{32}$P-labelled (73,000 cpm) at the 5'-end, was ligated to 1 pmole of PCR amplified Factor V oligonucleotide (Oligo FV, FIG. 6), using 5 units of T4 DNA ligase at 37° C. for 30 min. After ethanol precipitation, the sample was dissolved in UDG buffer and treated with 2 units of UDG at 37° C. for 30 min. The solution was then heat-treated at 65° C. for 10 min. and analyzed by 15% polyacrylamide gel electrophoresis (PAGE), 7 M urea, 0.5×TBE. The analysis showed that UDG cleavage produced four smaller fragments of the expected sizes, 20, 23, 26 and 29 nt, respectively.

EXAMPLE 2

Detection Principle (FIG. 2)

The detection principle is based upon that described above with regard to FIG. 2. Two different padlock probes A and B are used. One probe A has specificity to a template (below Factor V) and also exhibits a back-piece sequence which is complementary to the other probe B. Padlock probe B is tagged, e.g. with a fluorophore. Below it is demonstrated that (i) padlock probe A can be circularized in the ligation to its template consisting of a complementary oligonucleotide; (ii) padlock probe B can be circularized to padlock probe A; and (iii) padlock probes A and B can be circularized in the ligation to template.

(i) Circularization of Padlock Probe A in Ligation to Complementary Oligonucleotide 0.1 pmole of 92-mer padlock probe to Factor V (Padlock FV, FIG. 7) described in Example 1, padlock probe A, and 1.35 pmole of Factor V oligonucleotide (Oligo FV, FIG. 7) complementary to padlock probe A was ligated by 6 units of T4 DNA ligase at 37° C. for 30 min. The enzyme was then heat-inactivated at 60° C. for 10 min. A control reaction was performed without ligase. PAGE as in Example 1 showed that a catenated complex of padlock probe A and the complementary oligonucleotide was obtained.

(ii) Circularization of Padlock Probe B to Padlock Probe A 0.1 pmole of padlock probe A and 0.1 pmole of a padlock probe complementary to the back-piece of padlock probe A (Padlock αFV, FIG. 7), padlock probe B, were ligated as in (i) above. A control reaction was performed without ligase. PAGE as in Example 1 showed that a catenated complex of the two padlock probes A and B was obtained.

(iii) Circularization of Padlock Probe A to Padlock Probe B and Oligonucleotide 0.1 pmole of each of the padlock probes A and B and 1.35 pmole of Factor V oligonucleotide were ligated as in (i) above. A control reaction was performed without ligase. PAGE as in Example 1 showed that a catenated complex of the two padlock probes and oligo FV was obtained.

The invention is, of course, not restricted to the embodiments specifically described above and shown in the drawings, but many modifications and changes can be made within the scope of the present inventive concept as defined in the following claims.

The invention claimed is:

1. A method, wherein a target nucleic acid sequence is detected, comprising the following steps:
   a) providing an oligonucleotide probe immobilized to a solid support, the immobilized probe comprising two end parts having at least one 3'-end sequence and at least one 5'-end sequence, wherein one of said end parts is provided with a solid phase anchor by which the probe is immobilized to the support and wherein the other end part comprises at least one detectable function provided on a dissociable part of said probe,
   b) contacting the immobilized probe with a target nucleic acid sequence allowing the 3'-end and the 5'end of the immobilized probe to hybridize to at least substantially neighboring regions of said target nucleic acid sequence under hybridizing conditions;
   c) covalently connecting the ends of the hybridized oligonucleotide probe to each other to form a circularized structure;
   d) dissociating said dissociable part;
   so that if said probe is circularized in step c), the probe part comprising the detectable function becomes connected by catenation to the other probe part comprising the solid phase anchor and thereby connected to the support, and cannot be de-connected from the immobilized probe by said dissociating;
   but wherein if said probe is not circularized in step c), the probe part comprising the detectable function is not connected by catenation to the other probe part comprising the solid phase anchor, and hence is not connected to the support, and can be de-connected from the immobilized probe by said dissociating;
   e) separating non-connected detectable functions from the solid support by washing under denaturing conditions;
   f) detecting the target nucleic acid sequence by detecting the presence, and optionally, quantity and/or location of the connected detectable function, and
   wherein said probe comprises two padlock probes and said dissociable part is one of said padlock probes hybridizing to the other padlock probe which carries said solid phase anchor and hybridizes to the target nucleic acid sequence in step b).

2. The method according to claim 1, wherein one or both of the probe ends have at least two branches, and a detectable function is provided on each of the branches on one end part of said probe, the detectable functions being different and distinguishable from each other.

3. The method according to claim 1, wherein one probe end is linear and the other probe end is branched.

4. A method, wherein a target nucleic acid sequence is detected, comprising the following steps:
   a) providing an oligonucleotide probe immobilized to a solid support, the immobilized probe comprising two end parts having at least one 3'-end sequence and at least one 5'-end sequence, wherein one of said end parts is provided with a solid phase anchor by which the probe is immobilized to the support and wherein the other end part comprises at least one detectable function provided on a dissociable part of said probe,
   b) contacting the immobilized probe with a target nucleic acid sequence allowing the 3'-end and the 5'end of the immobilized probe to hybridize to at least substantially neighboring regions of said target nucleic acid sequence under hybridizing conditions;
   c) covalently connecting the ends of the hybridized oligonucleotide probe to each other to form a circularized structure;
   d) dissociating said dissociable part;
   so that if said probe is circularized in step c), the probe part comprising the detectable function becomes connected by catenation to the other probe part comprising the solid phase anchor and thereby connected to the support, and cannot be de-connected from the immobilized probe by said dissociating;

but wherein if said probe is not circularized in step c), the probe part comprising the detectable function is not connected by catenation to the other probe part comprising the solid phase anchor, and hence is not connected to the support, and can be de-connected from the immobilized probe by said dissociating;

e) separating non-connected detectable functions from the solid support by washing under denaturing conditions;

f) detecting the target nucleic acid sequence by detecting the presence, and optionally, quantity and/or location of the connected detectable function, and wherein said probe comprises two padlock probes and said dissociable part is one of said padlock probes, which hybridizes to the target nucleic acid sequence in step (b) and to the other padlock probe carrying said solid phase anchor.

5. The method according to claim 4, wherein said probe is designed to hybridize to the target nucleic acid sequence in step (b) to leave an interspace between the probe ends, at least one additional probe is provided which is designed to hybridize to the target nucleic acid sequence in said interspace, and said additional probe is covalently connected to the ends of the hybridized probe in step (c).

6. The method according to claim 4, wherein said probe is designed to hybridize to the target nucleic acid sequence in step (b) to leave at least one small gap between adjacent probe ends, and said gap is filled by an extension reaction prior to covalently connecting the probe ends in step (c).

7. The method according to claim 4, wherein said covalently connecting the probe ends is performed by enzymatic, ribozyme-mediated or chemical ligation.

8. The method according to claim 4, wherein said target nucleic acid is a DNA or RNA sequence.

9. The method according to claim 4, wherein said solid phase anchor is biotin and said oligonucleotide probe is immobilized via the biotin to a streptavidin-coated solid phase.

10. A method, wherein a target nucleic acid sequence is detected, comprising the following steps:

a) providing an oligonucleotide probe, said probe comprising two end parts having at least one 3'-end sequence and at least one 5'-end sequence, wherein one of said end parts is provided with a solid phase anchor for immobilization of said probe to a solid support and wherein the other end part comprises at least one detectable function and a cleavable site which lies between the detectable function and the solid phase anchor, b) contacting the probe with a target nucleic acid sequence allowing the 3'-end and the 5'end of said probe to hybridize to at least substantially neighboring regions of said target nucleic acid sequence under hybridizing conditions;

c) covalently connecting the ends of any hybridized oligonucleotide probe to each other to form a circularized structure;

d) immobilising said probe to a solid support by means of said solid phase anchor (i) before step b) or (ii) between steps c) and e);

e) cleaving the circularized and non-circularized oligonucleotide probe at the cleavable site between the detectable function and the solid phase anchor;

so that if said probe is circularized in step c), the probe part comprising the detectable function becomes covalently connected to the other probe part comprising the solid phase anchor and thereby connected to the support, and cannot be de-connected from the immobilized probe part by said cleaving;

but wherein if said probe is not circularized in step c), the probe part comprising the detectable function is not covalently connected to the other probe part comprising the solid phase anchor, and hence is not covalently connected to the support, and can be de-connected from the immobilized probe part by said cleaving;

f) separating non-connected detectable functions from the solid support by washing under denaturing conditions;

g) detecting the target nucleic acid sequence by detecting the presence, and optionally, quantity and/or location of the connected detectable function, and wherein said cleavable site is a disulphide or a deoxyuridine residue or a peptide residue or a nucleotide sequence susceptible to cleavage by endonuclease, wherein in step e), said cleaving of the oligonucleotide probe takes place using a cleaving agent being a reducing agent, a uracil DNA glycosylase, a peptidase or an endonuclease, respectively.

* * * * *